US00PP25407P3

(12) United States Plant Patent
Perathoner

(10) Patent No.: US PP25,407 P3
(45) Date of Patent: Apr. 7, 2015

(54) APPLE TREE NAMED 'GALA PERATHONER'

(50) Latin Name: *Malus domestica Borkh.*
Varietal Denomination: Gala Perathoner

(71) Applicant: Griba Baumschulgenossenschaft Landw. Gesellschaft, Terlan (IT)

(72) Inventor: Siegfried Perathoner, Leifers (IT)

(73) Assignee: Griba Baumschulgenossenschaft Landw. Gesellschaft, Terlan (IT)

( * ) Notice: Subject to any disclaimer, the term of this patent is extended or adjusted under 35 U.S.C. 154(b) by 39 days.

(21) Appl. No.: 13/815,140

(22) Filed: Feb. 4, 2013

(65) Prior Publication Data

US 2014/0223620 P1 Aug. 7, 2014

(51) Int. Cl.
*A01H 5/00* (2006.01)

(52) U.S. Cl.
USPC ..... Plt./162

(58) Field of Classification Search
USPC ..... Plt./162
See application file for complete search history.

(56) References Cited

PUBLICATIONS

UPOV-PLUTO: Plant Variety Database, 20140721, cultivar 'Gala Perathoner'.*

Community Plant Variety Office (CPVO) application for 'Gala Perathoner', Feb. 23, 2009, 15 pages.

"Le nuove mutazioni di Gala", *Rivista di Frutticoltura e di ortofloricoltura*, Anno LXXIV-N. 11, Nov. 2012, 2 pages.

* cited by examiner

*Primary Examiner* — Susan McCormick Ewoldt

(74) *Attorney, Agent, or Firm* — Myers Bigel Sibley & Sajovec, PA

(57) ABSTRACT

*Malus domestica* Borkh 'Gala Perathoner' variety is distinguished from the original mother plant 'Mitchgla' cultivar and other Gala varieties by a unique combination of characteristics including intense striped red over-colour that covers 95 to 100% of the fruit surface with two types of stripes being evident: light and dark red stripes that are partially overlapped creating an original attractive pattern, and prominent lenticels.

6 Drawing Sheets

Latin name of the genus and species: The Latin name of the genus and species of the plant variety disclosed herein is *Malus domestica* Borkh.

Variety denomination: The inventive cultivar of *Malus domestica* Borkh disclosed herein has been given the varietal denomination 'Gala Perathoner'.

BACKGROUND OF THE INVENTION

The present invention relates to a new and distinct Gala variety of apple trees named 'Gala Perathoner'. The new variety was discovered as a sport limb mutation on a Gala plant cultivar 'Mitchgla' (not patented), in a cultivated field in Ora area, Bolzano province, Italy. The mutated branch was identified some days before picking time and noticed because of the darker red-striped coloration of the fruits compared to the other fruits on the plant (FIG. 1).

The mutation was first asexually propagated in Spring 2003 and 15 trees were initially grown. The new variety 'Gala Perathoner' was first asexually reproduced by chip budding on M9 rootstocks of bud wood by one year old lateral branch of the mutated part of the mother 'Mitchgla' tree. The first asexually reproduced trees were located in Verona Province in an isolated apple trial field in "Gazzo Veronese" locality, managed by the applicant. The first observed fruiting of the propagated trees occurred in the 2005 season and confirmed the intensity of the fruit stripe red coloration and the stability of the mutation.

In the next years, many other trees have been asexually propagated, planted and evaluated in other locations in Bolzano province and Verona province. All the trees of 'Gala Perathoner' have been observed to remain true to type over successive asexually propagated generations and maintain the intensity of their characteristic stripe-red colour (FIG. 4).

SUMMARY OF THE INVENTION

The new variety 'Gala Perathoner' is distinguished from the original mother plant 'Mitchgla' cultivar and other Gala varieties by the following unique combination of characteristics: intense striped red over-colour that covers 95 to 100% of the fruit surface; two types of stripes that are evident: light and dark red stripes that are partially overlapped creating an original attractive pattern; and lenticels that are prominent.

In particular, the new variety can be distinguished from 'Mitchgla' in that the apples of 'Mitchgla', at ripening time, were partially red stripe over colored with evident larger stripes and less pronounced lenticels than 'Gala Perathoner', and the over color of 'Mitchgla' apple covered 50% of the apple surface with a light red color (Red RHS50A) compared to the dark striped over-color (RHS 53A) of 'Gala Perathoner', which covers more than 95% of the apple surface. The new variety can be distinguished from the 'Galaval' cultivar (U.S. Plant Pat. No. 19,909) by the evidence of stripes in 'Gala Perathoner' fruits and by a lighter red fruit colour (RHS 53A) compared to dark purple colour (RHS 59A) of 'Galaval' fruits.

The new variety can be distinguished from the 'Simmons Gala' cultivar (U.S. Plant Pat. No. 10,840) by the higher number and intensity of stripes of 'Gala Perathoner' fruits. In contrast to 'Simmons Gala', two colours of stripes can be identified in 'Gala Perathoner' fruits, light stripes (RHS 45A) and dark stripes (RHS 53A). The appearance of 'Gala Perathoner' fruit is less bright but with a darker red coloration than 'Simmons Gala' fruit (RHS 46A).

The new variety can be distinguished from the 'Burkitt Gala' cultivar (U.S. Plant Pat. No. 17,013) by the pattern of the fruit stripes and the darker coloured stripes of 'Gala Perathoner' fruit. Dark and light red stripes are alternated on 95-100% of the fruit skin of 'Gala Perathoner' and no or very few stripes show the yellow ground colour, while more yellow stripes are evident on 'Burkitt Gala' fruits. The lenticels are more evident on 'Gala Perathoner' fruit than 'Burkitt Gala' fruits.

The new variety can be distinguished from the 'Baigent' cultivar (U.S. Plant Pat. No. 10,016) by the finer stripes, the darker red over colour and the higher over colour coverage of 'Gala Perathoner' fruits.

The new variety can be distinguished from the 'Banning Gala' cultivar (U.S. Plant Pat. No. 13,753) by the more evident stripes and darker red over colour of 'Gala Perathoner' fruits.

Asexual reproduction of this new variety by grafting and budding onto rootstock shows that the foregoing and all other characteristics and distinctions remain true to form over successive asexually propagated generations.

BRIEF DESCRIPTION OF THE DRAWINGS

The colours of these illustrations may vary with lighting conditions and, therefore, colour characteristics of this new variety should be determined with reference to the observations described herein, rather than from these illustrations alone.

FIG. 4, profile; FIG. 5, calix eye; FIG. 6, stalk cavity.

DETAILED BOTANICAL DESCRIPTION

The following detailed description of the 'Gala Perathoner' variety is based on observations made during the 2012 growing season in a high density 'Gala Perathoner' planting field in Ora area, Bolzano Province (Italy).

Certain characteristics of this variety may change with changing environmental conditions (e.g., light, temperature, moisture), nutrient availability, or other factors. Quantified measurements are expressed as an average of measurements taken from a number of individual plants of the new variety. The measurements of any individual plant, or any group of plants, of the new variety may vary from the stated average. Colour descriptions and other terminology are used in accordance with their ordinary dictionary descriptions, unless the context clearly indicates otherwise. Colour designations are made with reference to The Royal Horticultural Society (R.H.S.) Colour Chart.

Figure 1:
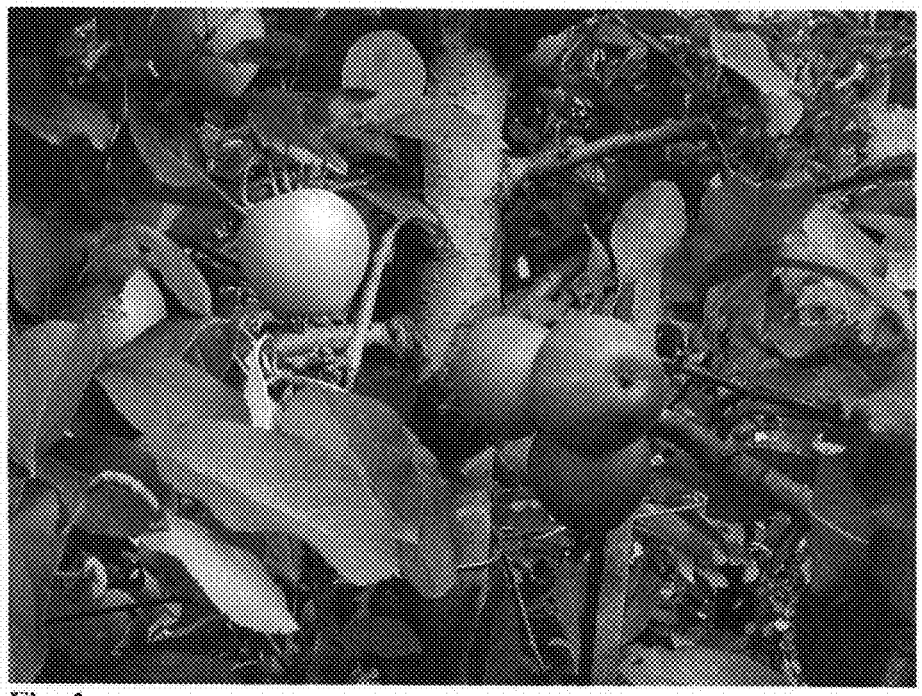
FIG. 1 illustrates the original mutated branch of Gala plant from which 'Gala Perathoner' has been identified and generated. The apples attached on the mutated branch are stripe-red coloured compared to the other apples on the trees.

Parentage: 'Gala Perathoner' variety originated by a sport limb mutation of a lateral branch of a Gala cultivar 'Mitchgla', identified in 2002 in a cultivated field of the Farm 'Perathoner' in Ora area, Bolzano province, Italy. The mutated branch was identified at the beginning of August, 10 days earlier than the picking time, and noticed because of the anticipated and strong stripe-red coloration of the fruits compared to the original 'Mitchgla' mother plant and the other 'Mitchgla' trees into the field (FIG. 1).

Figure 2:
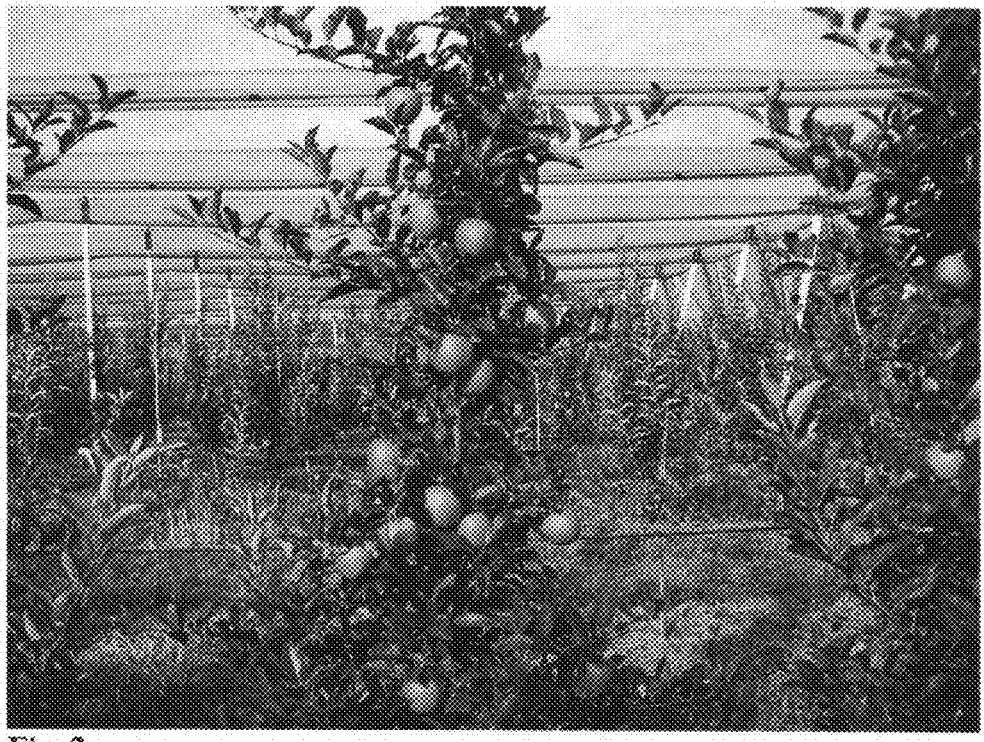
FIG. 2 and FIG. 3 illustrate 3 year old 'Gala Perathoner' trees of second generation with fruits at picking time.
Figure 3:
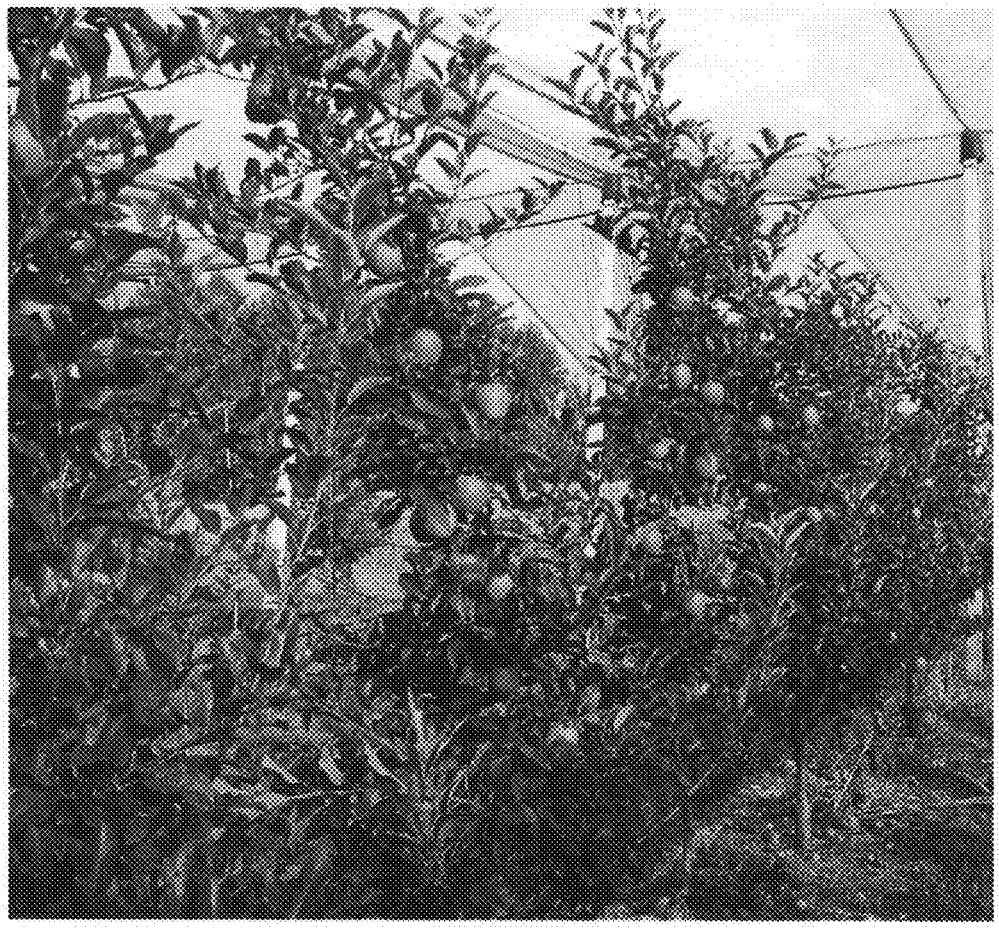

Tree: the trees described here are three-year-old trees grown on M9 rootstock deriving from the second generation vegetatively propagated 'Gala Perathoner' mutation. (FIGS. 2 and 3).

Vigour and overall shape: 'Gala Perathoner' trees on M9 rootstock show an upright ramified growth habit with medium vigour, similar to the other Gala clones.

*Height*.—2.60 m.

*Width*.—1.00 m.

Trunk: Medium stocky; diameter, 40 mm at 200 mm above the graft union; bark texture, smooth; bark colour, Grey RHS 201C; lenticels, evident horizontally elongated; lenticel colour, Black RHS 202C.

Primary branches: Basal branches emerge at 700 mm from the soil with an angle of about 70 to 90 degrees.

Two year old branches: Length, 500-600 mm; diameter measured at the base, 22 mm; crotch angle, 70 to 90 degree; colour Grey-Brown RHS 199C.

One-year old branches: Length, 325 mm; thickness, 5 mm; internode length, 31 mm; colour at middle of July, Greyed-Orange RHS 166A; pubescence, absent or very weak; number of lenticels per square centimetre, 8 to 10; lenticel shape, longitudinal elongated respect to shoot; lenticels colour Greyed-White RHS 156C.

Bearing: Annual, abundant, necessity of thinning, flower-buds principally on shoots, very low or not subjected to alternant bearing.

Hardiness: European hardiness zone 6, comparable to other Gala varieties.

Drought, disease and insect resistance: Susceptibility to classical apple disease comparable to other Gala varieties.

Leaves: Shape, elliptic; length, medium-long 105 mm; width, 58 mm; length/width ratio, 1.8; blade margins, crenate; apex, acute slightly acuminate; base shape, truncate; colour of upper surface, Green RHS 136A; colour of lower surface, Green RHS 138A; pubescence on lower surface, light; pubescence colour, White RHS N155A; leaf attitude in relation to shoot, outward (FIG. 2 and FIG. 3).

*Petiole*.—Length, medium 39 mm; thickness, medium 2.2 mm; colour, Yellow-Green RHS 147B; petiole pubescence, very weak, colour White RHS N155A.

*Stipules*.—Quantity, 2 opposite; shape, thin elongated; length 4 mm; colour, Yellow-Green RHS 147B.

Flowers: Flower buds (unopened flower): number per cluster, 5 to 6; length, 12 mm; diameter, 9 mm; shape, round-conical; colour, Red-Purple RHS N57D. Open flower: size, medium-small; diameter, 32 mm; pollination requirement varieties, 'Stark Delicious' (not patented), 'Golden Delicious' (not patented), 'Granny Smith' (not patented), 'Idared' (not patented), 'Summerred' (not patented) and other varieties.

Petals: Number per flower, 5; relative position of petal margins, slightly overlapping; shape, ovoid-elliptic; length, 15 mm; width, 12 mm; apex, rounded; base, conical pointed; margin, smooth; colour of upper surface, White RHS NN155C; colour of lower surface, White RHS NN155B.

Pistil: Size, medium 14 mm long; stigma colour, Yellow-Green RHS 145D; styles quantity, 5; style colour, Yellow-Green RHS 145B; ovary colour, Green RHS 143A.

*Anthers*.—Quantity 20 to 25 per flower; size, 2.1 mm; presence of pollen; colour of pollen, Yellow RHS 4B.

Sepals: Quantity, 5; shape, conical pointed; colour, Green RHS 143A.

Pedicel: Length 20 mm; diameter, 1.6 mm; colour, Green RHS 143A.

Bloom season: In 2012 at Ora area in Bolzano Province, Italy, blooming began the 29$^{th}$ of March; full bloom was the 2$^{nd}$ of April; finishing on the 7$^{th}$ of April.

Figure 4:
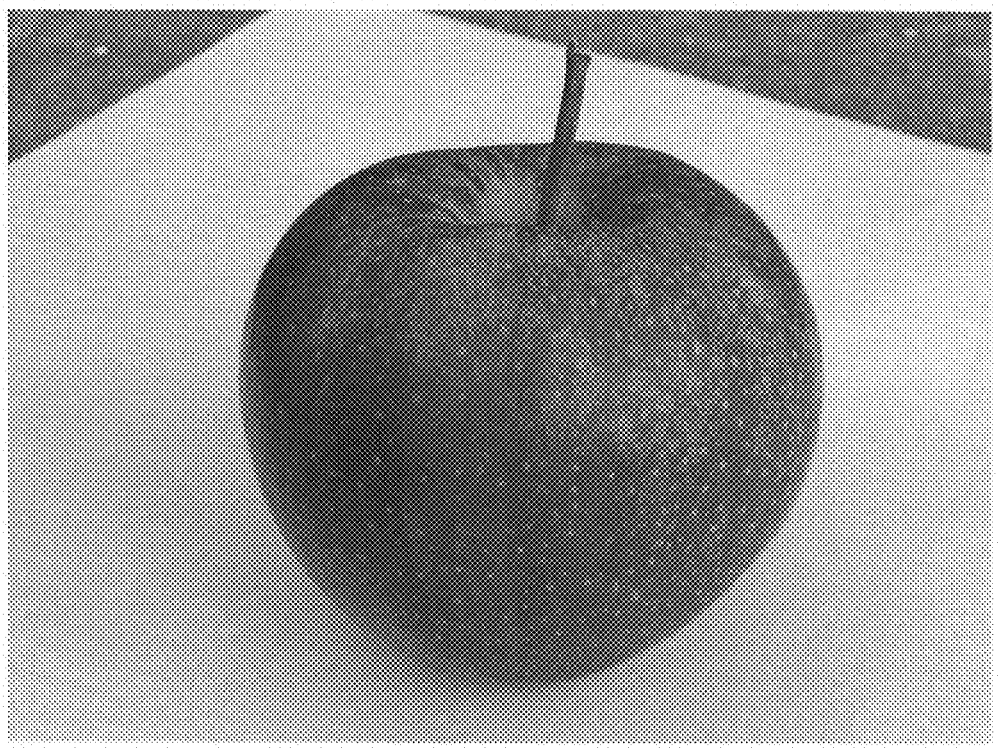
FIGS. 4-6 illustrate a 'Gala Perathoner' apple after harvesting.
Figure 5:
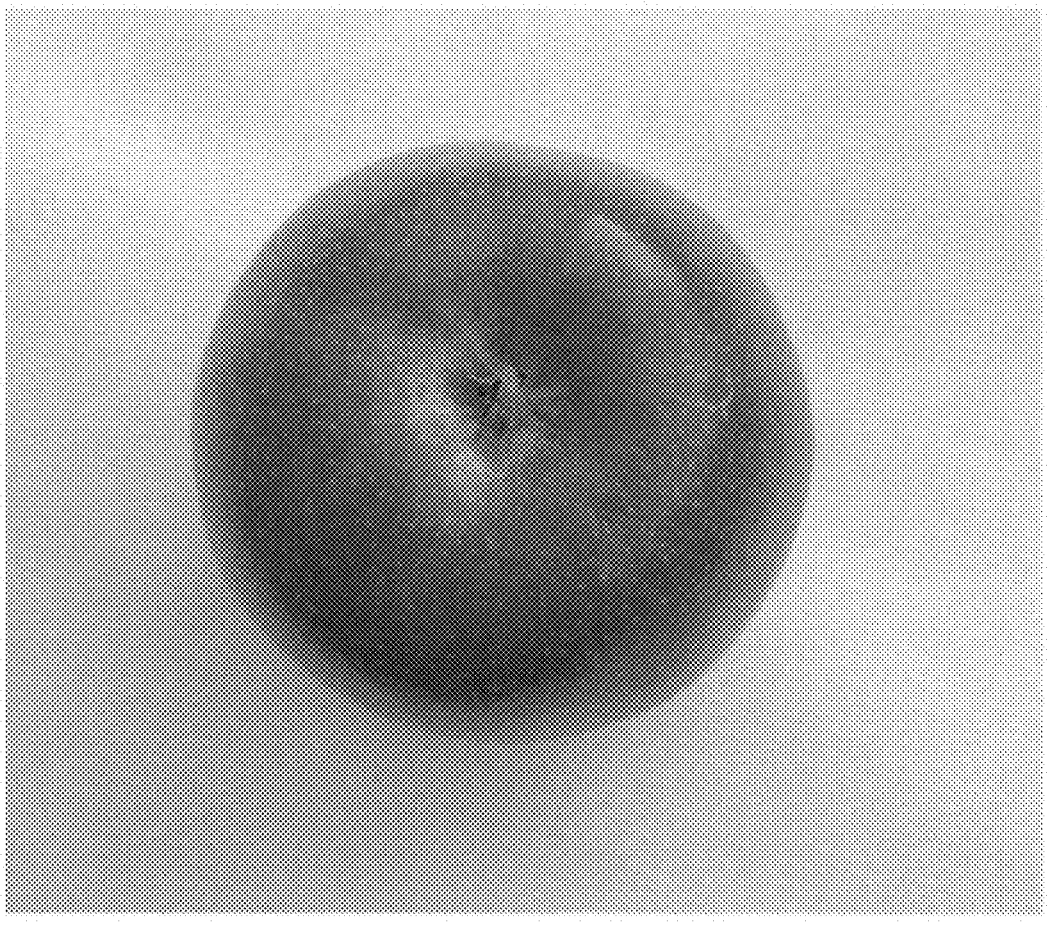
Figure 6:
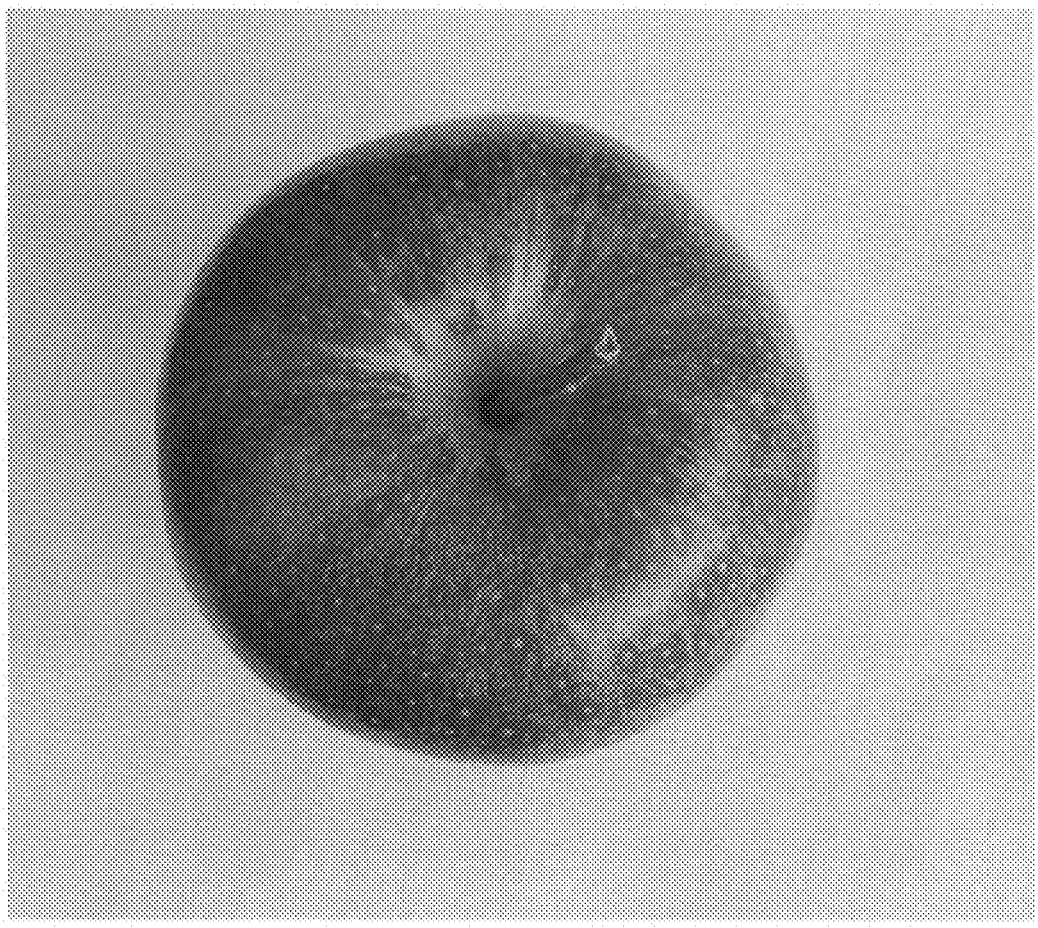

Fruit: Quantity per cluster, 1 to 3; size, medium; diameter (average of 50 typical fruits), 79 mm; weight, 211 g; ratio height/width, 1.18; general shape in profile, globose (FIG. 4); maximum diameter, in the middle; ribbing, absent; crowning, absent; depth of calix eye, 5 mm; width of calix eye, 4 mm; depth of calix end, 9 mm; width of calix end, 26 mm; depth of stalk cavity, 18 mm; width of stalk cavity, 25 mm; length of stalk, 29 mm; thickness of stalk, 2.2 mm; colour of stalk, Greyed-Red RHS 178B (FIG. 6); close sepals (FIG. 5), length of sepals, 6 mm.

Fruit skin: Sense to the touch, smooth, slightly waxy; bloom, absent or very weak; greasiness, absent or very weak; thickness, thin; russet around stalk cavity, present weak; russet around the calix eye, absent or very weak; number of cheeks per square cm, 5 to 7; shape of cheeks, round-stellate; size of cheeks, 0.5 mm; colour of cheeks, Greyed-Orange RHS 164D; russet around cheeks, present but very limited around cheek.

Fruit skin colour: Background colour, Yellow-Orange RHS 17D; pattern of over colour, striped with two types of stripes: light and dark stripes (FIGS. 4, 5 and 6); light stripes colour, Red RHS 45A; dark stripes colour, Red RHS 53A; frequency of stripes, mainly 5 to 10 stripes per centimetre; amount of over-colour, 95 to 100% fruit coverage; intensity of over-colour, brilliant red; appearance of stripes, the stripes run from the top to the bottom of fruit with borders between stripes not always strictly defined that create a nice and attractive effect of overlapping dark and light red colour.

Figure 7:
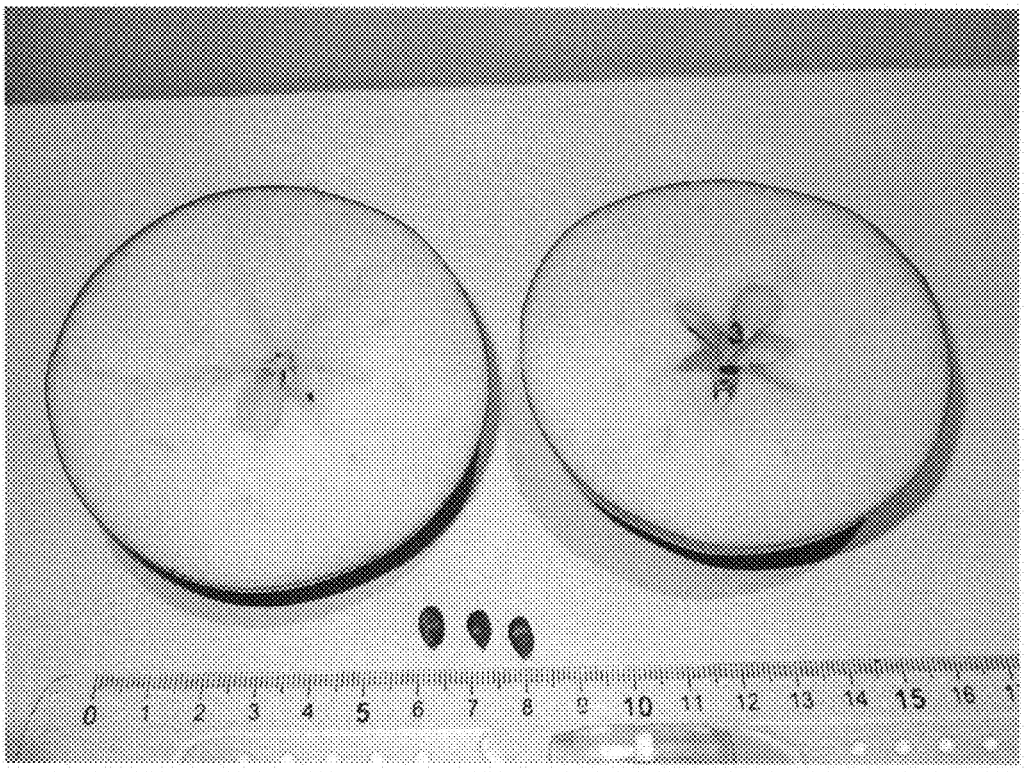
FIG. 7 illustrates the flesh of 'Gala Perathoner' on the equatorial section and the seeds.

Fruit flesh: Firmness, medium to firm; texture, fine; colour, Yellow-Orange RHS 18C (FIG. 7); flavour, sweet; at harvest time 12-12.5 Brix and 4.7-5.2 g/l acidity; aroma, good and intense aroma classical of the original 'Gala'; juiciness, moderately-juicy.

Fruit core: Vascular bundles evident; locules, five to six open; seeds, 1 to 2 per locule, shape of seed, oval elongated; colour of seeds, Greyed-Orange RHS 177A.

Fruit picking time: In 2012 at Ora area in Bolzano Province, Italy, the first picking of 'Gala Perathoner' began the 10$^{th}$ of August (30 days earlier than 'Golden Delicious') where the high coloration of this clone permitted to harvest 70% of apples, the second picking began the 17$^{th}$ of August. The market use of the fruit of 'Gala Perathoner' is in the fresh market.

What is claimed is:

1. A new and distinct tree of *Malus domestica* Borkh named 'Gala Perathoner', substantially as illustrated and described herein.

* * * * *

UNITED STATES PATENT AND TRADEMARK OFFICE

CERTIFICATE OF CORRECTION

PATENT NO. : PP25,407 P3
APPLICATION NO. : 13/815140
DATED : April 7, 2015
INVENTOR(S) : Perathoner It is certified that error appears in the above-identified patent and that said Letters Patent is hereby corrected as shown below:

In the specification

Column 3, Line 38: Please add the following sentence after "trees."
-- The age of the tree is 11 years. --

Column 3, Line 66 and Column 4, Line 1:
Please correct "field of the Farm 'Perathoner' in Ora area,"
to read -- field in Ora area, --

Column 4, Line 58:
Please correct "other varieties."
to read -- other varieties flowering in the same period except for Gala group. --

Signed and Sealed this
Thirteenth Day of October, 2015

Michelle K. Lee

Michelle K. Lee
*Director of the United States Patent and Trademark Office*